US010265199B2

(12) United States Patent
Chabloz

(10) Patent No.: US 10,265,199 B2
(45) Date of Patent: Apr. 23, 2019

(54) METHOD FOR PRODUCING A PROSTHETIC SLEEVE TO MEASURE

(71) Applicant: Pierre Chabloz, Saint Georges de Commiers (FR)

(72) Inventor: Pierre Chabloz, Saint Georges de Commiers (FR)

(73) Assignee: CHABLOZ COMPOSANTS, Seyssinet-Pariset (FR)

( * ) Notice: Subject to any disclaimer, the term of this patent is extended or adjusted under 35 U.S.C. 154(b) by 552 days.

(21) Appl. No.: 14/418,780

(22) PCT Filed: Jul. 31, 2013

(86) PCT No.: PCT/FR2013/000208
§ 371 (c)(1),
(2) Date: Jan. 30, 2015

(87) PCT Pub. No.: WO2014/020245
PCT Pub. Date: Feb. 6, 2014

(65) Prior Publication Data
US 2015/0289998 A1 Oct. 15, 2015

(30) Foreign Application Priority Data

Aug. 2, 2012 (FR) ...................................... 12 02169
Aug. 16, 2012 (FR) ...................................... 12 02244

(51) Int. Cl.
*B29C 51/00* (2006.01)
*A61F 2/80* (2006.01)
(Continued)

(52) U.S. Cl.
CPC .............. *A61F 2/80* (2013.01); *A61F 2/5046* (2013.01); *A61F 2/7812* (2013.01);
(Continued)

(58) Field of Classification Search
CPC ........ B29C 51/10; B29C 51/42; B29C 51/002
(Continued)

(56) References Cited

U.S. PATENT DOCUMENTS 5,258,037 A 11/1993 Caspers
5,480,455 A * 1/1996 Norvell ................ A61F 2/7812
2/904
(Continued)

FOREIGN PATENT DOCUMENTS

EP 1023012 B1 10/2003
EP 1961380 A1 8/2008
(Continued)

*Primary Examiner* — Christina A Johnson
*Assistant Examiner* — Xue Liu
(74) *Attorney, Agent, or Firm* — Oliff PLC

(57) ABSTRACT

The method for manufacturing a made-to-measure prosthetic sleeve from a thermoformable preform includes: providing a reduced positive mold corresponding to the copy of the shape of the stump of the residual limb reduced by 3 to 5% of all of the circumferences of the shape of the stump; providing a preform made from a thermoformable elastomer base, the preform presenting an open proximal end, a closed distal end, a uniform wall thickness and a hardness of more than 40 Shore A; placing the preform on the reduced positive mold to form a preform/mold assembly; shaping the preform by heating the preform/mold assembly to a temperature between 60° C. and 150° C.

12 Claims, 6 Drawing Sheets

(51) Int. Cl.
*A61F 2/50* (2006.01)
*A61F 2/78* (2006.01)
*B29L 31/00* (2006.01)
*B29K 75/00* (2006.01)
*B29K 83/00* (2006.01)
*B29C 51/10* (2006.01)
*B29K 9/06* (2006.01)
*B29K 105/00* (2006.01)

(52) U.S. Cl.
CPC .... *B29C 51/002* (2013.01); *A61F 2002/5053* (2013.01); *A61F 2210/0071* (2013.01); *A61F 2240/00* (2013.01); *A61F 2240/002* (2013.01); *B29C 51/10* (2013.01); *B29C 2791/006* (2013.01); *B29K 2009/06* (2013.01); *B29K 2075/00* (2013.01); *B29K 2083/00* (2013.01); *B29K 2105/0085* (2013.01); *B29L 2031/7532* (2013.01)

(58) Field of Classification Search
USPC .................................. 264/292, 222, 223, 227
See application file for complete search history.

(56) References Cited

U.S. PATENT DOCUMENTS

| | | | |
|---|---|---|---|
| 5,824,111 | A | 10/1998 | Schall et al. |
| 6,764,631 | B1 | 7/2004 | Laghi |
| 6,918,936 | B2 | 7/2005 | Hellberg |
| 2002/0165619 | A1* | 11/2002 | Hellberg ............... A61F 2/5046 623/36 |
| 2008/0188948 | A1 | 8/2008 | Flatt |
| 2010/0016991 | A1* | 1/2010 | Hellberg ............... A61F 2/5046 623/33 |

FOREIGN PATENT DOCUMENTS

| | | |
|---|---|---|
| FR | 1532625 A | 7/1968 |
| FR | 2903294 A1 | 1/2008 |
| WO | 98/48741 A1 | 11/1998 |

* cited by examiner

METHOD FOR PRODUCING A PROSTHETIC SLEEVE TO MEASURE

BACKGROUND OF THE INVENTION

The object of the invention is to provide a method for manufacturing a made-to-measure prosthetic sleeve for the residual limb of an amputee from a thermoformable preform.

STATE OF THE ART

For amputees who have lost an end of a limb such as an arm or a leg, commonly called residual limb, the use of a sleeve between the prosthesis and the residual limb is commonly used to reduce chafing and to enhance skin-friendly contact of the prosthesis.

As represented in FIGS. 1 and 2, a prosthesis 1 comprises a socket 2 which is designed to receive the stump 3 of a residual limb 4 and to secure it to enable it to press on prosthesis 1. A sleeve 5 is generally arranged between stump 3 and socket 2. Sleeve 5 facilitates fitting of stump 3 in prosthesis 1 and provides greater comfort for the amputee.

During walking with a prosthesis, socket 2 enables transmission of the forces during the pressing phase and activation of prosthesis 1 by stump 3 of residual limb 4.

Sockets 2 are called "partial-contact" sockets when the end of stump 3 remains free, "suction" sockets when there is a depression chamber with a valve or "total-contact" sockets when the whole of stump 3 is in close contact with socket 2.

As represented in FIG. 2, sleeve 5 can advantageously be adherent to snugly follow the shape of stump 3 thereby preventing friction between stump 3 and sleeve 5.

Sleeve 5 has to promote a uniform distribution of the pressure or a decreasing distribution of the latter from the distal end to the proximal end of stump 3 exerted by residual limb 4 on socket 2 of prosthesis 1 to prevent trophic disorders and other complications due to poor arterial circulation in residual limb 4.

Sleeve 5 further has to present a very good adherence to ensure that it remains on stump 3 during prosthetic walking and to be dermatologically acceptable in order to prevent problems related to cutaneous intolerance.

The most commonly used adherent sleeves are made from polymer material in the form of an expanded foam such as polyurethane or silicone foams. Generally speaking, the polymer material used is highly flexible, presenting a hardness of less than 10 Shore A.

Current methods for manufacturing custom-made sleeves from polyurethane or silicone are performed either by impregnation of a fabric by the polymer material or by casting of the polymer material between a positive mould having exactly the shape of stump 3 and a rigid shell forming a negative counter-mould. The rigid shell acts as outer mould and defines the thickness of sleeve 5. The polymer material is then cast by gravity or pushed to enable it to reach the bottom of the mould.

These two techniques present a certain number of disadvantages. They are difficult to reproduce and give a sleeve 5 having an irregular thickness that is difficult to control. Sleeve 5 obtained in this way thus presents securing properties that are difficult to control and to reproduce.

In the document U.S. Pat. No. 6,764,631, the authors propose a sleeve and a manufacturing method which overcome these drawbacks. The method consists in providing a positive mould exactly matching the shape of the stump on which a thermoformable tubular preform is placed and in then moulding said tubular preform by heating. The thermoformable preform described is made from an elastomer of gel type, formulated by mixing of a styrene-ethylene-styrene triblock copolymer with a mineral oil. The sleeve obtained in this way nevertheless presents the disadvantage of being sticky and of creating adherences with the walls of the socket making it difficult to insert the stump coated with the sleeve in the socket of the prosthesis. The sleeve made from gel elastomer further presents a low hardness and a low tear resistance. The authors therefore propose covering the thermoformable coating with a fabric to increase the lifetime of these sleeves and to facilitate fitting of the stump in the socket. This solution is not satisfactory as it presents the disadvantage of introducing an additional step and an additional manufacturing cost of the sleeve.

In the documents EP-B-1023012 and U.S. Pat. No. 6,918,936, the authors propose a prosthetic sleeve made from a thermoformable elastomer material and its manufacturing method. The thermoformable elastomer material is preferably a Styrene-Ethylene-Butylene-Styrene (SEBS) copolymer advantageously characterized by a hardness of about 5 to 40 Shore A and an elongation at rupture of about 600 to 1200%. The method for its part consists in providing a positive mould exactly matching the shape of the stump on which a tubular coating made from thermoformable elastomer material is placed and in moulding said tubular coating by heating to a temperature of about 60° C. or more. The sleeve obtained in this way nevertheless presents the disadvantage of being generally malleable and therefore greatly deformable. The specifically exemplified SEBS elastomer material, DRYFLEX© 500120 marketed by Nolato Elastoteknik, Torekov (SE), in particular presents a hardness of 12 Shore A. The authors therefore propose to increase the strength of the sleeve by adding a material of greater hardness, thereby increasing the thickness of the sleeve. Furthermore, the manufacturing method involves the use of a positive mould exactly matching the shape of the stump, adhesion of the sleeve on the stump therefore being linked solely to the elastic properties of the sleeve and the fact that it sometimes retracts slightly during the thermal forming step. The sleeve and manufacturing method described in the document U.S. Pat. No. 6,918,936 do not therefore in any way enable precise control of the distribution of securing of the sleeve on the stump.

A hitherto unsatisfied requirement therefore exists to provide a prosthetic sleeve in particular enabling an extremely precise control of the distribution of securing of the sleeve on the stump.

OBJECT OF THE INVENTION

The object of the invention is to provide a method for manufacturing a made-to-measure prosthetic sleeve which remedies the shortcomings of the prior art.

More particularly, the invention relates to a method for manufacturing a made-to-measure prosthetic sleeve that is durable, comfortable, and guarantees an improved drainage and a better circulation at the level of the vascular and nervous bundles of the residual limb while at the same time ensuring a very good adherence between the stump and the sleeve. The prosthetic sleeve obtained according to the method for manufacturing of the present invention in particular enables extremely precise control of distribution of securing of the sleeve on the stump.

This object tends to be achieved by means of a method for manufacturing a made-to-measure prosthetic sleeve from a thermoformable preform comprising the following successive steps:

providing a reduced positive mould corresponding to the copy of the shape of the stump of the residual limb reduced by 3 to 5% of all of the circumferences of the shape of the stump, providing a preform made from a thermoformable elastomer base, said preform presenting an open proximal end, a closed distal end, a uniform wall thickness and a hardness of more than 40 Shore A, preferably greater than 42 Shore A, and even more preferably greater than 45 Shore A, placing the preform on the reduced positive mould to form a preform/mould assembly, shaping the preform by heating the preform/mould assembly to a temperature comprised between 60° C. and 150° C., preferably between 90° C. and 120° C.

BRIEF DESCRIPTION OF THE DRAWINGS

Other advantages and features will become more clearly apparent from the following description of particular embodiments of the invention given for non-restrictive example purposes only and represented in the appended drawings, in which.

DESCRIPTION OF PARTICULAR EMBODIMENTS

Figure 1:
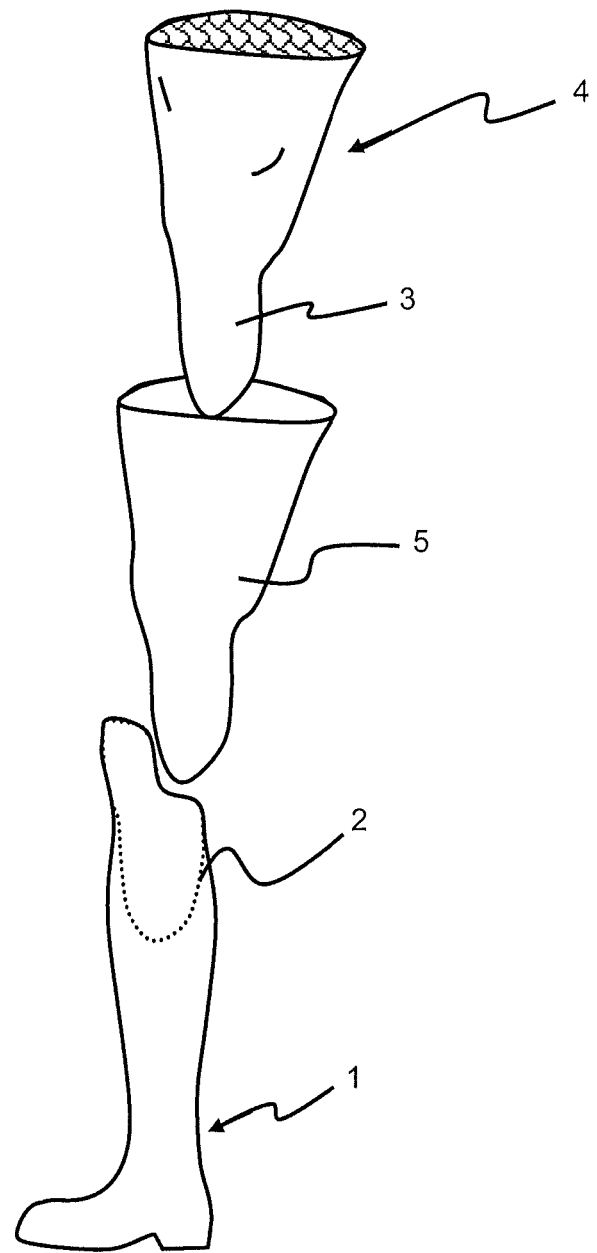
FIG. 1 represents a prosthesis with a sleeve according to the prior art, schematically and in perspective view.
Figure 2:
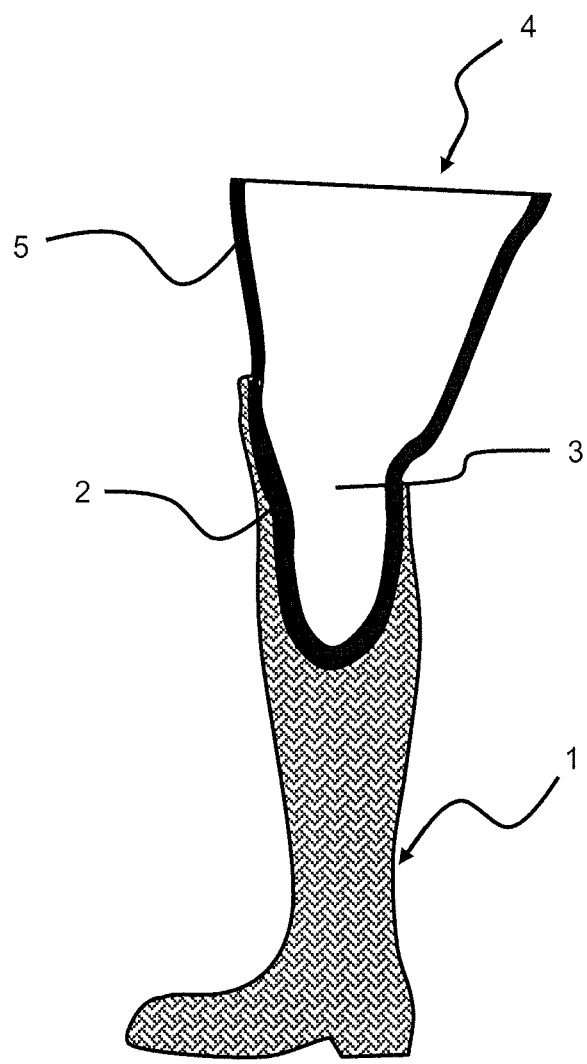
FIG. 2 represents a prosthesis with a sleeve according to the prior art, schematically and in cross-section.

According to a particular embodiment represented in FIGS. 3 to 7, a method for manufacturing a made-to-measure prosthetic sleeve 5 for a residual limb 4 of an amputee is implemented from a particular thermoformable preform 8.

In surprising and totally unexpected manner, it has been discovered that the associated use of a particular reduced positive mould and of a given thermoformable preform in a method for manufacturing a prosthetic sleeve enables a prosthetic sleeve to be achieved which fits the stump perfectly while applying a precisely defined securing force on said stump.

The reduced positive mould 7 according to the invention corresponds to the perfect copy 6 of the shape of stump 3 of residual limb 4 reduced by 3 to 5% of all of its circumferences.

Figure 3:
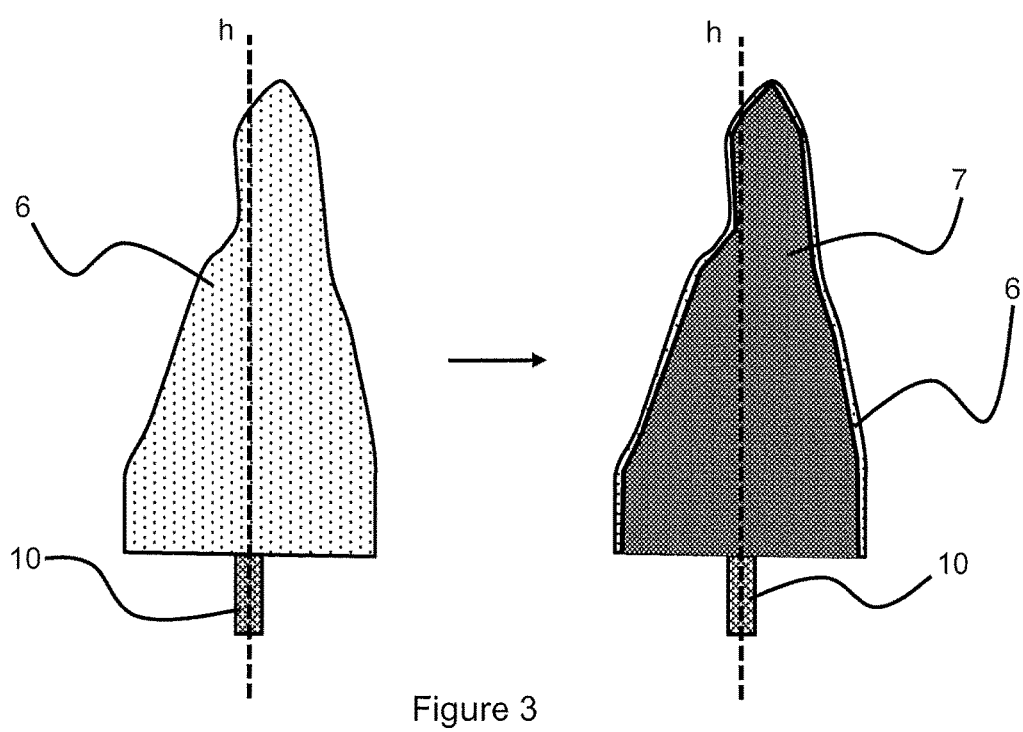
FIGS. 3 to 7 represent different steps of a method for manufacturing according to a particular embodiment, schematically and in cross-section.

What is meant by "3 to 5% reduction of all of the circumferences of copy 6 of the shape of stump 3" is either reduction of all of the circumferences of copy 6 of the shape of stump 3 by a given value, comprised between 3 and 5% of the value of said circumferences, the latter being perpendicular to the axis h represented in FIG. 3, or reduction of all of the circumferences of copy 6 of the shape of stump 3 in regular manner in a proximo-distal direction with respect to stump 3 of residual limb 4, the distal reduction being greater than the proximal reduction, the distal reduction being a maximum of 5% and the proximal reduction being a maximum of 3%.

The reduced positive mould 7 can be manufactured by means of any known method, for example from a 3D image of the shape of the stump 3 obtained by a laser scanner, the image, which is a copy 6 of the shape of stump 3, then being reduced to the required dimensions thereby enabling the reduced positive mould to be produced 7. Copy 6 of the shape of stump 3 can also be made by means of the measuring device described in the document EP-B-1961380.

Reduced positive mould 7 can be made from resin, or preferably from plaster or polyurethane foam, from a negative mould of copy 6 of the shape of stump 3 reduced to the required dimensions.

In order to facilitate implementation of the method for manufacturing according to the invention, reduced positive mould 7 can have a mandrel 10 arranged in the centre of the base, not used for thermoforming, of reduced positive mould 7. Mandrel 10 enables subsequent positioning and securing of reduced positive mould 7.

Preform 8 used in the method is made from a thermoformable elastomer base, i.e. an elastomer able to be shaped by heating. What is meant by "thermoformable elastomer base" is the fact that preform 8 is constituted in substance by the thermoformable elastomer, which does not exclude the presence of possible additives commonly used in the field.

Thermoformable polymers are commercially available with a wide range of elasticity and hardness. Preform 8 according to the invention is constituted by a base formed by a polymer with a hardness greater than 40 Shore A, preferably greater than 42 Shore A, and even more preferably greater than 45 Shore A. It has in fact surprisingly been discovered that only the selected thermoformable elastomers of the invention enable a prosthetic sleeve to be obtained that is solid, durable, not too flexible, which matches the shape of the stump perfectly and enables a perfectly well-defined securing force to be exerted on said stump. The Applicant observed in particular that a hardness less than or equal to 40 Shore A regularly led to tearing of the made-to-measure prosthetic sleeve and/or a too weak adherence of the sleeve to the stump.

The thermoformable elastomer can in particular be formed by a base comprised of Styrene-Ethylene-Butylene-Styrene copolymer, noted SEBS.

Figure 4:
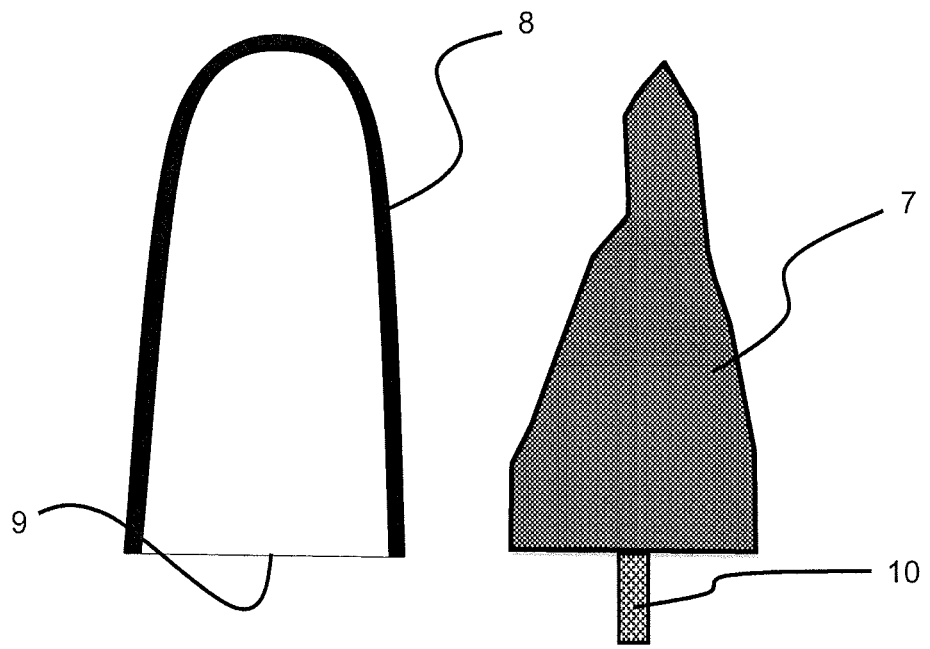

As represented in FIG. 4, preform 8 presents an open proximal end 9 and a closed distal end. Opening 9 of the proximal end is preferably circular and presents a diameter matching the dimension of stump 3 of residual limb 4.

Preform 8 further presents a uniform wall thickness. The wall thickness preferably varies from 2 to 4 mm.

Preform 8 can be obtained by means of any method well known to the person skilled in the art. According to a preferred embodiment, thermoformable preform 8 is obtained by plastic injection. Such an injection technique enables a wide range of sizes and dimensions to be provided with a high reproducibility and a uniform wall thickness.

Figure 5:
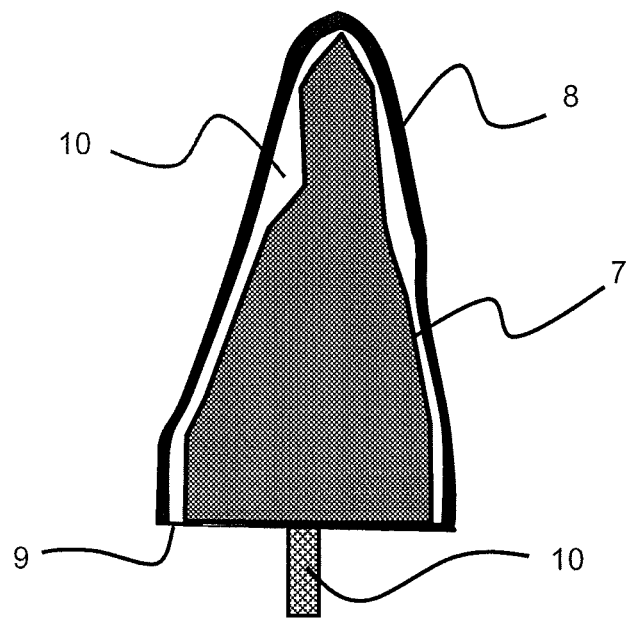

As represented in FIG. 5, preform 8 is then placed on reduced positive mould 7 thereby forming a preform/mould assembly.

The size of preform 8, in particular of opening 9, is chosen in such a way as to easily match the shape of reduced positive mould 7. The size of preform 8 can advantageously be chosen slightly smaller than that of reduced positive mould 7 in order to exert a sufficient pressure to keep preform 8 secured on reduced positive mould 7.

As illustrated in FIG. 5, the wall of preform 8 snugly follows at least a part of reduced positive mould 7, generally leaving uncovered areas 10 on account of the difference of shape between preform 8 and reduced positive mould 7.

Figure 6:
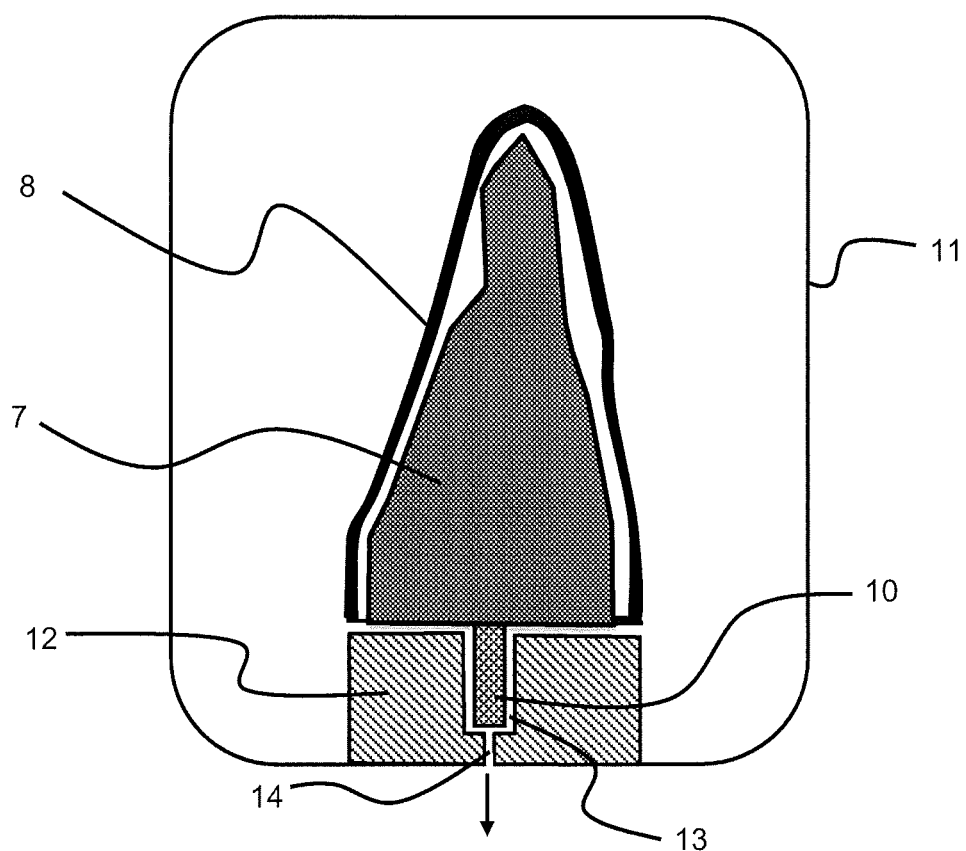
Figure 7:
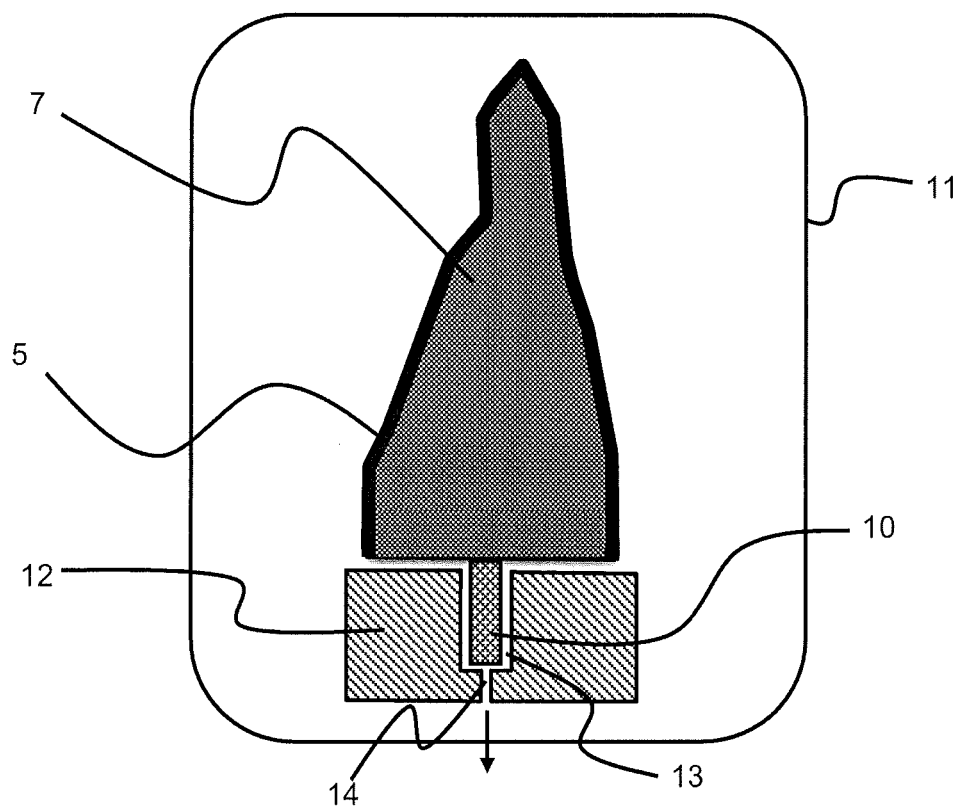

As represented in FIG. 6, the preform/mould assembly is then placed in a furnace 11, placing preferably being performed using a support 12. Support 12 is conventionally provided with a housing 13 designed to receive mandrel 10.

According to a preferred embodiment of the present invention, a device exists enabling a negative pressure to be created between reduced positive mould 7 and preform 8 (not shown). Creation of a vacuum by means of the negative pressure creation device enables suction of the air to be performed, for example through a channel 14 formed in support 12 of reduced positive mould 7, in fluidic communication with the air comprised between reduced positive mould 7 and preform 8 (downward-pointing arrow in FIG. 6). Preform 8 is then sucked against the walls of reduced positive mould 7.

The suction step if performed prevents the formation of bulges at the level of uncovered areas 10 (FIG. 5) and improves the precision of adjustment of prosthetic sleeve 5 and the uniformity of its thickness.

Preform 8 is then shaped by heating of the preform/mould assembly to a temperature comprised between 60 and 150° C., preferably between 90° C. and 120° C. The heating step is preferably performed for a period of 30 to 90 min, preferably from 50 to 75 min. The thermoformable elastomer forming preform 8 is deformed due to the effect of the heat to then perfectly follow the shape of reduced positive mould 7.

The made-to-measure prosthetic sleeve 5 is then obtained, after returning to ambient temperature and, if applicable, a return to atmospheric pressure between reduced positive mould 7 and preform 8. The made-to-measure prosthetic sleeve 5 is removed from the mould by means of any known technique, for example by cutting of the proximal end of prosthetic sleeve 5 and partial turning of said sleeve 5.

According to a preferred embodiment of the present invention, prosthetic sleeve 5 is coated with polyurethane on its outer surface. Polyurethane does in fact make it possible to easily roll and unroll prosthetic sleeve 5 on and off stump 3 guaranteeing a low adherence of the different portions of the outer surface of sleeve 5 with one another. Fitting and removal of prosthetic sleeve 5 on and from stump 3 are thereby made easier. Preferably, the polyurethane used on prosthetic sleeve 5 is obtained by reaction of xylene, isobutyl alcohol and diacetone. Such a polyurethane therefore provides a good trade-off between the adherence of different portions of the outer surface of sleeve 5 to one another and the adherence of sleeve 5 with prosthesis 1.

According to a preferred embodiment, sleeve 5 comprises a binding primer between the thermoformable polymer and the polyurethane coating. Preferably, the binding primer comprises xylene, vinyl acetate resin, butyl acetate, ethyl acetate and a mixture of chlorinated polyolefin/chlorobenzene/epoxydized oil. In particular, a binding primer comprising the above-mentioned substances in the following respective maximum quantities presented excellent results: max. 30%, max. 5%, max. 50%, max. 20%, max. 20%, (percentages by weight).

According to a particular embodiment, preform 8 is coated with polyurethane, and possibly with a binding primer between the thermoformable polymer and the polyurethane coating.

Prosthetic sleeve 5 can be secured to prosthesis 1 by means of a sealing ring (not shown) secured to socket 2 as described in Patent FR2903294. Alternatively, prosthetic sleeve 5 can conventionally be associated with an automatic valve or by a terminal securing device arranged at the end of sleeve 5 and clipping into a mechanism located at the bottom of socket 2 (not shown).

Prosthetic sleeve 5 formed in this way presents improved adherence and securing qualities and a longer lifetime than traditional sleeves. The securing obtained from prosthetic sleeve 5 is perfectly uniform or decreasing from the distal end of stump 3 to the proximal end of stump 3 thereby guaranteeing an excellent drainage of residual limb 4. Indeed, as the distal end of stump 3 is clamped tighter than the proximal end, the lymphatic and sanguineous drainage of stump 3 is thereby improved.

Furthermore, the good adherence of sleeve 5 prevents perspiration and stabilizes stump 3 in volume, thus increasing, for example for a leg prosthesis 1, the walking perimeter of the amputee.

Furthermore, the method for manufacturing is easy to implement and inexpensive. The use of a thermoformable elastomer, preferably formed by a SEBS copolymer base, enables industrial production of a made-to-measure prosthetic sleeve 5 to be envisaged with a high yield and at low cost.

The invention claimed is:

1. A method for manufacturing a made-to-measure prosthetic sleeve comprising the successive following steps:
   providing a reduced positive mould corresponding to a copy of the shape of a stump of a residual limb defining a plurality of circumferences from a distal end to a proximal end wherein all circumferences of the reduced positive mould are reduced by 3 to 5% as compared to all corresponding circumferences of the copy of the shape of the stump,
   providing a preform made from a thermoformable elastomer, said preform presenting an open proximal end, a closed distal end, a uniform wall thickness and a hardness of more than 40 Shore A,
   placing the preform on the reduced positive mould to form a preform/mould assembly, and
   shaping the preform by heating the preform/mould assembly to a temperature between 60° C. and 150° C. to obtain the made-to-measure prosthetic sleeve.

2. The method according to claim 1, wherein the thermoformable elastomer presents a hardness of more than 42 Shore A.

3. The method according to claim 2, wherein the thermoformable elastomer presents a hardness of more than 45 Shore A.

4. The method according to claim 1 further comprising, after placing the preform on the reduced positive mould, lowering a pressure between the reduced positive mould and the preform.

5. The method according claim 1, wherein shaping the preform is performed for a period of 30 to 90 min.

6. The method according to claim 5, wherein shaping the preform is performed for a period of 50 to 75 min.

7. The method according to claim 1, wherein the preform has a uniform wall thickness of 2 to 4 mm.

8. The method according to claim 1, wherein the thermoformable elastomer is a Styrene-Ethylene-Butylene-Styrene copolymer.

9. The method according to claim 1, wherein the made-to-measure prosthetic sleeve is coated with polyurethane.

10. The method of claim 1, wherein each circumference is a homothety of the circumference of the stump.

11. The method according to claim 1, wherein all circumferences of the reduced positive mould are reduced by a constant value between 3% and 5%.

12. The method according claim 1, wherein all circumferences of the reduced positive mould are reduced in a regular manner in a proximo-distal direction with respect to the stump of the residual limb, and a reduction in the distal end being greater than a reduction in the proximal end.

* * * * *